(12) United States Patent
Katscher et al.

(10) Patent No.: US 7,653,228 B2
(45) Date of Patent: Jan. 26, 2010

(54) ORGAN-SPECIFIC BACKPROJECTION

(75) Inventors: Ulrich Katscher, Norderstedt (DE);
Thomas Koehler, Norderstedt (DE);
Thomas Schmidt, Norderstedt (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 822 days.

(21) Appl. No.: 10/510,005

(22) PCT Filed: Mar. 24, 2003

(86) PCT No.: PCT/IB03/01122

§ 371 (c)(1),
(2), (4) Date: Aug. 12, 2005

(87) PCT Pub. No.: WO03/083778

PCT Pub. Date: Oct. 9, 2003

(65) Prior Publication Data

US 2006/0013459 A1  Jan. 19, 2006

(30) Foreign Application Priority Data

Mar. 30, 2002  (DE)  ................ 102 14 254

(51) Int. Cl.
*G06K 9/00* (2006.01)
(52) U.S. Cl. .................................... 382/131
(58) Field of Classification Search ............... 382/128, 382/131
See application file for complete search history.

(56) References Cited

U.S. PATENT DOCUMENTS

| | | | | |
|---|---|---|---|---|
| 5,834,779 A | * | 11/1998 | Shao et al. | 250/363.03 |
| 6,490,476 B1 | * | 12/2002 | Townsend et al. | 600/427 |
| 6,553,356 B1 | * | 4/2003 | Good et al. | 706/15 |
| 6,590,213 B2 | * | 7/2003 | Wollenweber | 250/363.03 |
| 7,191,109 B2 | * | 3/2007 | Ohba et al. | 703/6 |
| 7,218,766 B2 | * | 5/2007 | Eberhard et al. | 382/132 |

(Continued)

FOREIGN PATENT DOCUMENTS

JP  WO01/59477  *  8/2001

(Continued)

OTHER PUBLICATIONS

Schmidlin et al., "Iterative reconstruction of PET images using high-overrelaxation single-projection algorithm", 1997, Phys. Med. Biol., 569-582.*

(Continued)

*Primary Examiner*—Vikkram Bali
*Assistant Examiner*—Katrina Fujita

(57) ABSTRACT

A method for selective imaging of body structures includes acquiring first image data set by a first tomography method, acquiring a second image data set by a second tomography method which has a resolution which is higher than that of the first method, the image data of the first and the second image data set coinciding at least partly in space, reconstructing an image from the first image data set, and selecting the image data to be reconstructed from the first image data set using the second image data set. In order to achieve a higher imaging quality while using a low-resolution tomography method, image reconstruction of the image data selected from the first image data set at least one image region to be imaged is selected from the second image data set, and subsequently the image reconstruction is calculated from the image data of the first image data set which are situated in the selected image region.

20 Claims, 3 Drawing Sheets

U.S. PATENT DOCUMENTS

2003/0128801 A1* 7/2003 Eisenberg et al. ............. 378/19
2003/0156684 A1* 8/2003 Fessler ....................... 378/210

OTHER PUBLICATIONS

Delaney et al., "Multiresolution Tomographic Reconstruction Using Wavelets", Jun. 1995, IEEE Trans. on Image Processing, vol. 4, No. 6, 799-813.*

Bidaut, Luc M.; Accurate Registration of Various Medical Imaging Modelities; IEEE, 1991, pp. 1233-1237.

Lipinski, B., et al.; Expectation Maximization Reconstruction of Positron Emission Tomography Images Using Anatomical MR. Information; IEEE, 1997, pp. 129-136.

Vollmar, ST., et al.; Iterative Reconstruction of Emission Tomography Data with A-Priori-Information; IEEE, 1999, pp. 1560-1561.

Tu, Kao-Yin, et al.; Empirical Studies of Cross-Reference Maximum Likelihood Estimate Reconstruction; Biomedical Engineering, 2001, pp. 1-7.

Yong Zhang, et al.; Incorporating MRI Region Information into SPECT Reconstruction Using Joint Estimation; IEEE, 1995, pp. 2307-2310.

* cited by examiner

ORGAN-SPECIFIC BACKPROJECTION

This application claims the benefit of German Application No. 102 14 254.8 filed 30 Mar. 2002 and PCT Published Application No. WO 03/083778 filed 24 Mar. 2003.

The invention relates to a method for the selective imaging of body structures, in which method
- a first image data set is acquired by means of a first tomography method,
- a second image data set is acquired by means of a second tomography method which has a resolution which is higher than that of the first method, the image data of the first and the second image data set coinciding at least partly in space,
- an image is reconstructed from the first image data set, and
- the image data to be imaged is selected by means of the second image data set.

The invention also relates to a device for the selective imaging of body structures in conformity with the described method and to a computer program which is to be executed on a computer and comprises programming means for executing the described steps of the method.

Many tomography methods, notably tomography methods intended for nuclear medicine, such as SPECT (Single Photon Emission Computed Tomography) or PET (Positron Emission Tomography) methods, have the advantage that they provide the viewer of the tomographically formed image with information which goes beyond pure morphology and that in some cases they also visualize physiological processes. Such tomography methods have the drawback, however, that they have only a low spatial resolution so that often only a very poor imaging quality is achieved, notably for fine structures.

In order to avoid this drawback it is known to combine said tomography method with a further tomography method. The second tomography method then images the same region as the previously described tomography method having the low resolution. On the basis of the second tomography method, having a higher resolution, the viewer can then select a given region of interest from the overall image; very exact selection (so-called segmentation) is then possible because of the high resolution of the second method. Subsequently, that region of the low-resolution tomography image, produced by the first, low-resolution tomography method, which corresponds to the selected region of the high-resolution tomographic image is associated therewith by way of image registration, and exclusively this region is imaged. A method of this kind is described in the article "Iterative Reconstruction of Emission Tomography Data with A Priori Information", Vollmar St. et al., Transactions on Medical Imaging, 199.

This type of combination of two tomography methods has the drawback that the original image acquired by means of the low-resolution tomography method is reconstructed in a conventional manner and that the selection of a detail of this image by means of the high-resolution method takes place only at a later stage. For the conventional reconstruction of the image, the acquired image data are backprojected regularly; during such backprojection the signals measured during the image acquisition by way of forward projection are distributed along the relevant projection line across the entire image region. Because of this distribution across the entire image region, the signals become unsharp and the distance-to-noise ratio becomes small. Experts in this field refer to this phenomenon as "smearing".

Such smearing is particularly disadvantageous when an iterative method is used for the backprojection, because the smearing and the large image region to be measured necessitate a large number of iterations, thus prolonging the required calculation time and effort.

Therefore, it is an object of the invention to provide a method which enables a higher imaging quality to be achieved for a low-resolution tomography method. It is also an object of the invention to provide a device and a computer program for carrying out said method.

The object is achieved in accordance with the invention in that for the image reconstruction from the first image data set
- first at least one image region to be imaged is selected from the second image data set, and
- subsequently the image reconstruction is calculated from the image data of the first image data set which are situated in the selected image region.

Therefore, the method in accordance with the invention does not calculate a backprojection across the entire image region during the image reconstruction. Instead, an image region which is of interest to the viewer is selected in advance. This selection is performed on the basis of image data which have been acquired by means of a second tomography method having a resolution which is higher than that of the first tomography method. It is notably possible to select regions of the image which contain the object to be imaged or parts thereof. Furthermore, it is also possible to select a number of regions which may also be coherent, for example, vascular systems.

The backprojection of the image data across the selected image region ensures that the image values are not smeared across the entire image region, but only across a smaller image region, that is, the selected image region. It is thus achieved that the signal-to-noise ratio (SNR) is increased and the quality of the images of the structures to be imaged is enhanced.

The method in accordance with the invention is advantageous notably when the first tomography method is a nuclear-medical tomography method, notably a SPECT method or a PET method. According to such methods, a contrast medium is administered to the patient prior to the tomographic acquisition of the image data. This contrast medium concentrates in given structures of the body, possibly in dependence on given physiological processes, and is imaged with a high contrast by the nuclear medical tomography method. SPECT and PET then have only a low spatial resolution of from approximately 5 to 15 mm. In order to enhance the image quality, use can notably be made of a magnetic resonance tomography method or an X-ray tomography method (MR and CT, respectively). These tomography methods have a resolution in the range of from 0.5 to 1 mm. The use of the method in accordance with the invention is advantageous in particular when a combined CT/PET system or another tomography apparatus combining other tomographic methods is used for the tomographic imaging.

According to an advantageous version of the method the selection of the image region is performed by means of an automatic segmentation method.

In addition to the manual segmentation by the viewer, for example, by defining image boundaries or by selecting image corner points, notably automatic selection methods are advantageously used. According to the automatic selection methods, for example, a selection of the image elements to be imaged can be carried out on the basis of their image values (for example, grey values). For example, it is possible to select given body tissues on the basis of the image values of a computed tomography X-ray image (so-called HU values), said body tissues then being imaged or excluded from imaging. Furthermore, it is feasible for an automatic segmentation method to select regions which have the same or a similar image value and are coherent. Conventional segmentation methods, for example, the so-called regional growing method, can then be used. It may also be arranged that other methods, such as morphological opening or the like, are used for the automatic selection of an image region.

The method in accordance with the invention may ensure in particular that the necessary association of the image data of the first and the second image data set with one another, that is, the so-called registration, is simplified or accelerated by associating exclusively image data of the first image data set which are to be imaged with the second image data set.

It is particularly advantageous to use the method in accordance with the invention when the image reconstruction is carried out by way of iterative backprojection. An iterative calculation then takes place in principle in such a manner that the difference is formed between intermediate results of an image calculation which is periodically performed in the same manner is formed and that the quality of the calculated image is evaluated on the basis of the value of the difference between two successive calculation cycles. Normally speaking, a limit value (convergence criterion) to be reached is then defined.

Because the distance between the signal and the noise value is increased from the very start of the method in accordance with the invention, the method in accordance with the invention enables a reduction of the number of iteration steps required until a convergence criterion is met, that is, in comparison with the conventional method with smearing across the entire image region. Analogously, when the number of iteration steps in the method in accordance with the invention is kept the same as in conventional methods, the image quality of the image formed by means of the method in accordance with the invention can be enhanced in comparison with the image quality of the image reconstructed in a conventional manner.

A further aspect of the invention concerns a device for the selective imaging of body structures, which device includes first tomographic image data acquisition means, second tomographic image data acquisition means, having a resolution which is higher than that of the first tomographic image data acquisition means, means for image reconstruction by backprojection of an image, notably from a first image data set which has been acquired by means of the first tomographic image data acquisition means, and selection means for selecting at least one region of the image data to be imaged, preferably by selection of one or more regions of an image which has been derived from the second image data set. The backprojection means co-operate with the selection means in such a manner that during the backprojection of the image data exclusively the image data are projected which are situated in the selected image region which was selected, by way of the second image data set, by the selection means.

Finally, a last aspect of the invention concerns a computer program with programming means for making a computer carry out the method of claim 1 when the computer program is executed on a computer.

A preferred embodiment of the invention will be described in detail hereinafter with reference to the Figures. Therein:

Figure 1:
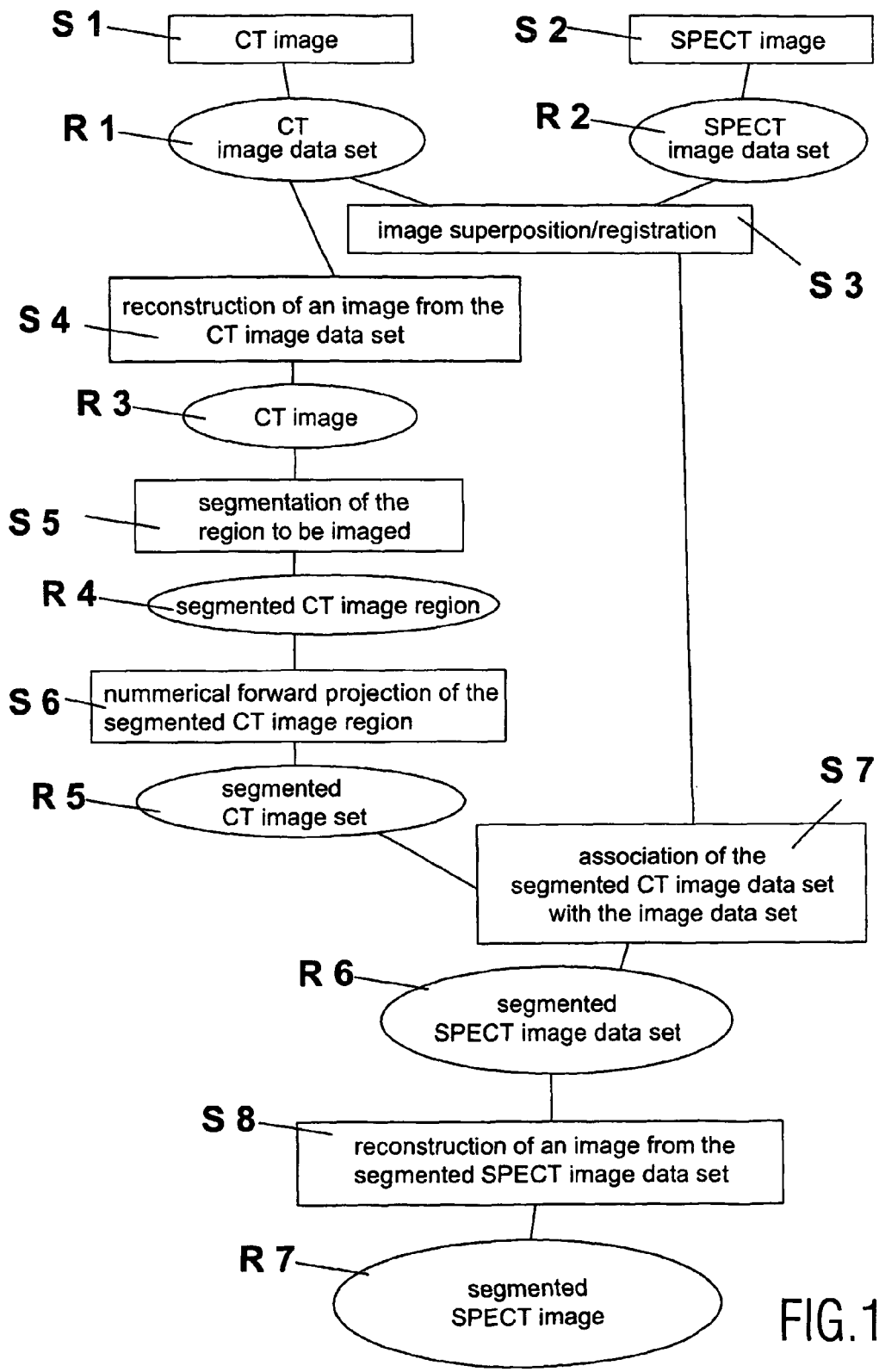
FIG. 1 shows a flow chart of a method in accordance with the invention.

As is shown in FIG. 1, in conformity with the preferred version of the method in accordance with the invention first a computed tomography image S1 of a body region is formed; for this purpose several slice images of this body region are acquired at a given distance from one another. This computed tomography image yields a CT image data set R1. Before or after the computed tomography image acquisition, a contrast medium is administered to the patient and a SPECT image S2 is formed, resulting in a SPECT image data set R2. The SPECT image S2 is preferably formed for the same body region and while using the same distance between the slice planes as for the CT image S1.

For the CT image data set R1 and the SPECT image data set R2 there is performed an image superposition or registration operation S3 in which the image data of the CT image data set R1 which are situated in the same geometrical position as the image data of the SPECT image data set R2 are associated with one another. Known methods, for example, fiducial markers can be used for such association. The CT image S1 and the SPECT image S2 need not necessarily cover an identical image region, but it suffices when the two images overlap in the region to be imaged. Furthermore, it is not necessary either for the spacing of the slices of the two images to be the same; it is also feasible that the distance between the slices of one image amounts to an integer multiple of the distance between the slices of the other image.

An image S4 is then reconstructed from the CT image data set R1; customary methods, such as iterative or analytic backprojection, can be used for this purpose. In the CT image R3 thus formed a segmentation of the region S5 to be imaged is performed. This segmentation can take place in a direction orthogonal as well as in a direction parallel to the projection direction, notably simultaneously in both directions. For example, a region to be imaged can be defined by setting a plurality of corner points of a region to be imaged or by drawing a boundary line around a region. It is also possible to select a plurality of regions to be imaged which are connected to one another or not. Furthermore, it is feasible for the segmentation to be executed automatically by the selection of image elements having a given range of image values or by the selection of coherent regions having a similar range of image values, for example, by way of the so-called region growing method. Furthermore, it is feasible to select structures in the image which are smaller or larger than a given value; customary methods, such as the morphological opening method, can be used for this purpose. It is also feasible to remove one or more image regions from the region to be imaged by means of a filtering operation.

The segmented CT image R4 thus formed is converted into a segmented CT image data set R5 by way of a numerical forward projection S6. During this step, the selected image elements, that is, the segmented region to be imaged, can be associated again with the image data of the original CT image data set in a simplified manner.

The image data of the segmented CT image data set are associated with the image data of the SPECT image data set in a next step S7, resulting in a segmented SPECT image data set R6. This segmented SPECT image data set R6 contains only the image data which are of relevance for the region to be imaged as selected on the basis of the CT image data set. In a further step S8 an image is reconstructed from the segmented SPECT image data set, that is, preferably by iterative backprojection of the segmented SPECT image data set. During this iterative backprojection, the image data is smeared only across the region to be imaged, so regularly across a region which is substantially smaller than the overall image region, thus enhancing the signal-to-noise ratio. The image R7 thus reconstructed has sharper edges and contains more contrast. This reduces the number of iteration steps required for an image whose quality is substantially equivalent to that of an image obtained by means of a conventional reconstruction technique, meaning that the required calculation time and effort are less. Analogously, when the number of iteration steps is the same as that of the conventional method, that is, while spending the same calculation time and calculation effort, an image of significantly higher quality can be formed.

Figure 2:
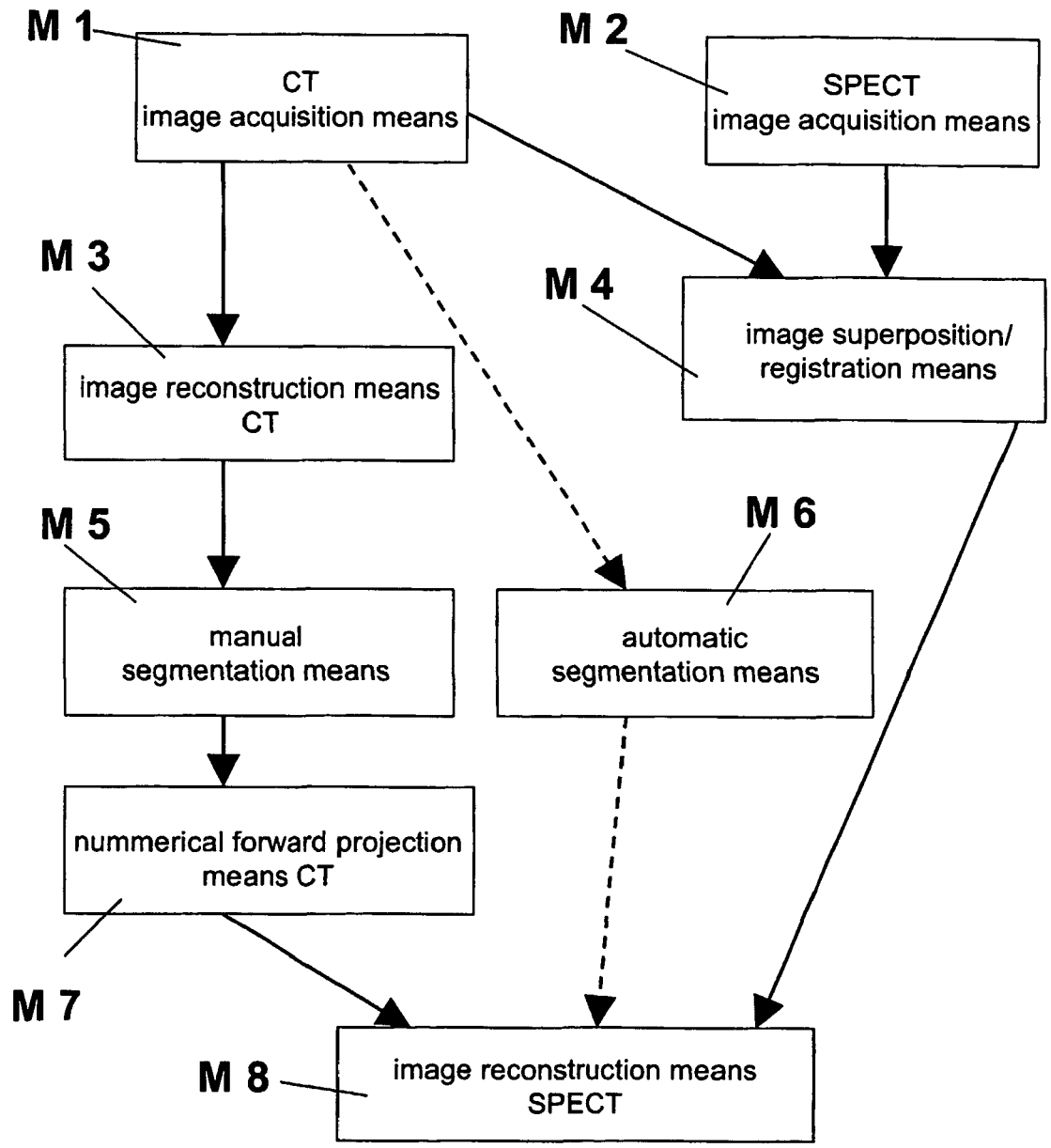
FIG. 2 is a diagrammatic representation of the co-operation of the means of a device in accordance with the invention.

FIG. 2 is a diagrammatic representation of the construction of the device in accordance with the invention and of the programming means of the computer program in accordance with the invention.

The device comprises CT image acquisition means M1 and SPECT image acquisition means M2 which co-operate with image superposition or registration means M4. The CT image acquisition means M1 co-operate with image reconstruction means M3 for the CT image, which means form a CT image from the CT image data set. This CT image is segmented by means of manual segmentation means M5 which are controlled by a user of the device, thus selecting a region to be image.

The manual segmentation means co-operate with means for the numerical forward projection M7 of the selected CT image elements which form an image data set from the segmented image.

Alternatively, as is denoted by the dashed lines in FIG. 2, the CT image acquisition means can co-operate with automatic segmentation means M6 which automatically select given data on the basis of preset parameters or parameters which can be influenced by the user of the device.

The image data selected by means of the automatic segmentation means M6 or the image data produced by means of the numerical forward projection means, co-operate with image reconstruction means M8 for the SPECT image data. The image reconstruction means for the SPECT image data co-operate with the image superposition/registration means so as to associate the selected CT image data with the corresponding, geometrically identically situated SPECT image data.

Alternatively it may also be arranged to perform the image superposition or registration by means of the image superposition means M4 only at an instant after a manual (M5) or automatic (M6) segmentation, and hence also selection of the image elements to be imaged, has taken place. In that case there is no superposition of image regions or registration of image data which are not situated in a region to be imaged.

The image reconstruction means SPECT M8 form a high-quality nuclear medical image of the segmented image region from the selected image data.

Figure 3:
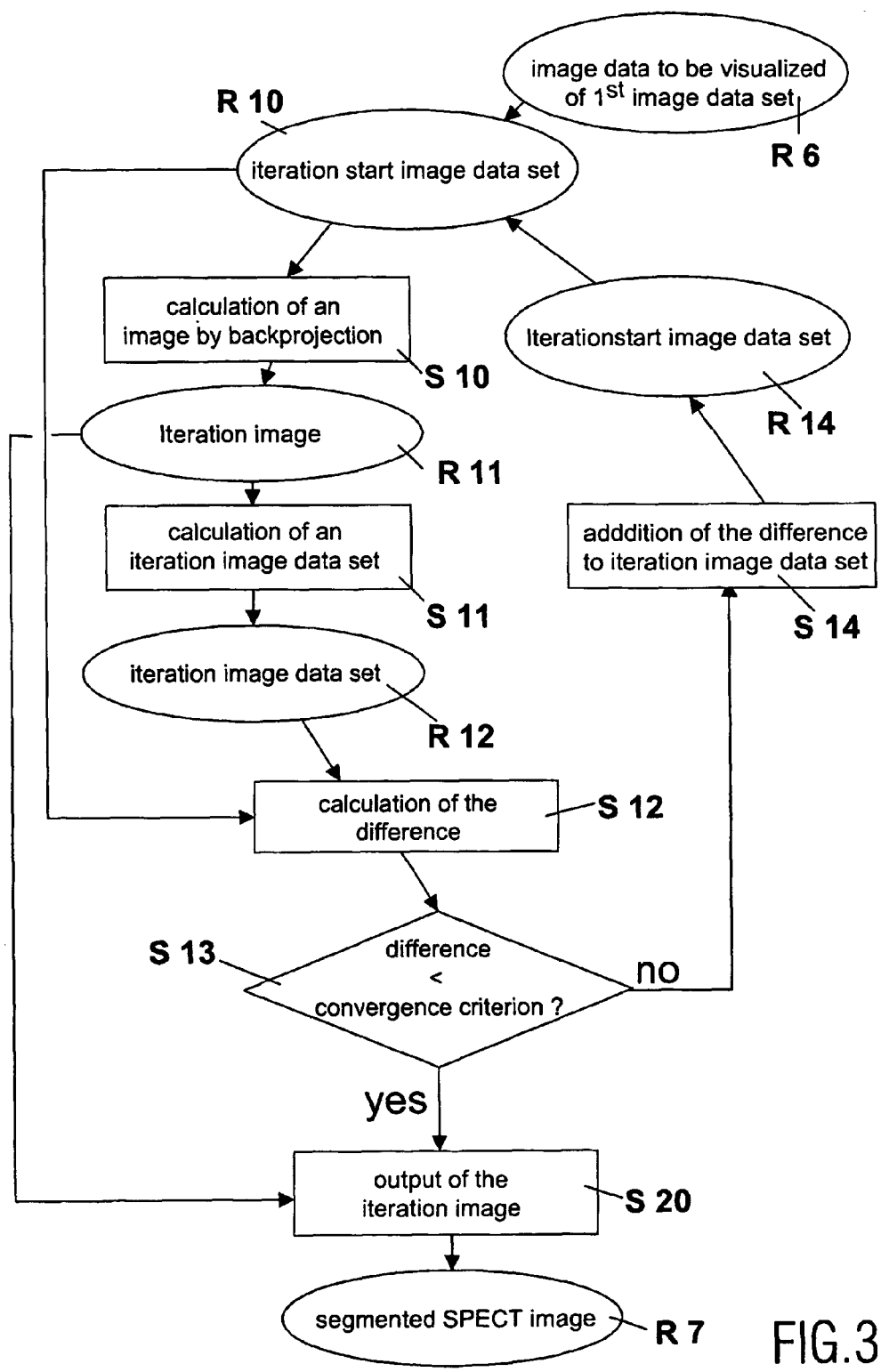
FIG. 3 shows a flow chart of a method for iterative backprojection.

The reconstruction of an image from the segmented SPECT image data set S8 by way of iterative backprojection will be described with reference to FIG. 3. The iteration consists in that first, in a backprojection S10, an iteration image R11 is calculated by backprojection of the image data to be imaged of the first image data set R6, selected on the basis of the second image data set or the image R1, R3, after which an iteration image data set R12 is numerically formed from this iteration image R11 in a calculation step S11. This iteration image data set R12 thus represents the result of a numerical forward projection S11 of the calculated image. Subsequently, a difference is formed S12 between the numerically formed iteration image data set R12 and the first image data set R10. This difference is a measure of the deviation between the iteration image data set R12 and the iteration start image data set R10. If this difference is particularly small S13, the calculated image does not constitute a significant qualitative improvement relative to the initially calculated image. In this case the iterative calculation process is terminated and the calculated image R11, R7 is output via an output S20.

When the difference does not drop below a predetermined value (the convergence criterion), however, the difference is added S14 to the iteration image data set S11 and a new iteration start image data set R14 is calculated. Using this calculated iteration start image data set R14, representing the new iteration start mage data set R10, subsequently an iteration operation is started again, at the end of which the difference is again used for evaluating the convergence and, should the converge criterion not be satisfied, the difference is again added to the iteration image data set R12 so as to form an iteration start image data set R14.

The above iteration steps are repeated until the convergence criterion is satisfied and the image R11 last calculated is output to the viewer as a segmented SPECT image R7.

The invention has been described with reference to the preferred embodiments. Modifications and alterations may occur to other upon reading and understanding the preceding detailed description. It is intended that the invention be construed as including all such modifications and alterations insofar as they come within the scope of the appended claims of the equivalents thereof.

The invention claimed is:

1. A device for selective imaging of body structures, which device includes:
   selection means for selecting a portion of a lower resolution first image data set situated in a selected image region based on a higher resolution second image data set; and
   a backprojection means co-operating with the selection means for reconstructing a first tomographic image exclusively from the portion of the first image data set which is situated in the selected image region.

2. The device as claimed in claim 1, wherein the selecting means includes:
   an automatic segmenting means which segments a second image reconstructed from the second image data set, the selected portion of the first image data corresponding to the segmented region of the second image.

3. The device as claimed in claim 2, further including:
   registration means for registering the first image data set and the second image data set.

4. A method for selectively imaging body structures, comprising the steps of:
   using a first tomography method to acquire a first image data set from a first spatial region;
   using a second tomography method to acquire a second image data set, the second tomography method having a higher resolution than the first tomography method and the second image data set containing image data that at least partly coincides in space with image data of the first image data set; and
   reconstructing the second image data set into a second tomographic image;
   segmenting the second tomographic image to define a selected image region;
   segmenting the first image data set in accordance with the selected image region segmented from the second image to define a segmented first image data set;
   reconstructing a first tomographic image exclusively from the segmented first image data set.

5. The method as claimed in claim 4, wherein the reconstructing step includes:
   backprojecting the segmented first segmented image data set into a first iterative image;

calculating a first iterative image data set from the first iterative image;

calculating a difference between the segmented first image data set and the first iterative image data set;

adding the difference to the segmented first image data set to generate a corrected first segmented image data set; and reconstructing the corrected segmented first image data set to generate the first tomographic image.

6. The method as claimed in claim 5, further including:

backprojecting the corrected segmented first image data set into a further iterative image;

calculating a further iterative image data set from the further iterative image;

calculating a difference between the corrected segmented first image data set and the further iterative image data set;

adding the difference to the corrected segmented first image data set.

7. The method for selectively imaging body structures, comprising the steps of:

using a first tomography method to acquire a first image data set;

using a second tomography method to acquire a second image data set, the second tomography method having a higher resolution than the first tomography method and the second image data set containing image data that at least partly coincides in space with image data of the first image data set; and reconstructing an image from the first image data set;

wherein data from the first image data set used in the reconstructing step is selected using the second image data set;

wherein the reconstructing step further comprises the steps of:

selecting a region smaller than the whole region to be imaged from at least one region represented in the second image data set; and calculating the image reconstruction from image data in a region represented in the first image data set that corresponds to the selected region represented in the second image data set.

8. The method as claimed in claim 7, wherein the reconstructing step further includes:

segmenting the first image data set to generate a segmented first image data set that contains only image data which are of relevance to the selected region;

reconstructing the segmented first image data set that contains only the image data of relevance to the selected region to generate a first tomographic image of the selected region.

9. The method as claimed in claim 8, wherein the reconstructing step includes iteratively:

backprojecting the corrected segmented first image data set into a further iterative image;

calculating a further iterative image data set from the further iterative image;

calculating a difference between the corrected segmented first image data set and the further iterative image data set;

adding the difference to the corrected segmented first image data set.

10. The method as claimed in claim 7, wherein the image reconstruction is calculated only from a portion of the first image data set that contributes to the selected region.

11. A method of selecting imaging body structures comprising:

acquiring a first image data set from a first spatial region with a tomographic nuclear medical imaging apparatus;

acquiring a second image data set from a second spatial region with a second tomographic imaging apparatus, the first and second spatial regions coinciding at least partially in space;

reconstructing the second image data set into a second image;

segmenting the second image to define a segmented second image;

forward projecting the segmented second image to form a segmented second image data set;

associating the segmented second image data set with the first image data set to form a segmented first image data set;

reconstructing the segmented first image data set into a segmented first image.

12. The method as claimed in claim 11, wherein the nuclear medical technique includes SPECT or PET.

13. The method as claimed in claim 11, wherein the segmenting step is performed by an automatic segmentation routine.

14. The method as claimed in claim 11, wherein reconstructing the segmented first image data set is carried out by way of iterative backprojection.

15. The method as claimed in claim 14, wherein the iterative backprojection includes:

(a) backprojecting the segmented first image data set to form an iteration image;

(b) numerically forming an iteration image data set from the iteration image, (c) determining a difference between the segmented first image data set and the iteration image data set, (d) adding the difference to the segmented first image data set; and (e) iteratively repeating steps (a), (b), (c), and (d) until at least one convergence criterion is satisfied.

16. The method as claimed in claim 15, wherein the convergence criteria includes the difference dropping below a predetermined convergence value.

17. The method according to claim 11, further including:

reconstructing the first image data set into a first image;

registering the at least one of: (1) the first and second images and (2) the first and second image data sets.

18. The method as claimed in claim 11, wherein the segmenting step identifies a selected region of the body structures and the associating step selects portions of the first image data set corresponding to the selected region.

19. The method as claimed in claim 18, wherein in the reconstructing step, the reconstructed segmented first image represents the selected region of the body structures.

20. The method as claimed in claim 19, wherein the reconstructing step includes iterative backprojection of the segmented first image data set, such that during the backprojection, backprojected image data is smeared only across the selected region.

* * * * *